United States Patent
Stern et al.

(10) Patent No.: US 9,078,618 B2
(45) Date of Patent: Jul. 14, 2015

(54) METHODS AND SYSTEMS FOR PATIENT ALIGNMENT FOR NUCLEAR MEDICINE IMAGING

(75) Inventors: Eli Stern, Givataim (IL); Deborah Ruth Zelnik, Tirat Hacarmel (IL); Ruth Katz, Binyamina (IL)

(73) Assignee: General Electric Company, Schenectady, NY (US)

(*) Notice: Subject to any disclaimer, the term of this patent is extended or adjusted under 35 U.S.C. 154(b) by 1009 days.

(21) Appl. No.: 12/915,623

(22) Filed: Oct. 29, 2010

(65) Prior Publication Data

US 2012/0108952 A1    May 3, 2012

(51) Int. Cl.
  *A61B 6/00*    (2006.01)
  *A61B 6/03*    (2006.01)
  *A61B 6/04*    (2006.01)

(52) U.S. Cl.
  CPC ............. *A61B 6/4241* (2013.01); *A61B 6/037* (2013.01); *A61B 6/0407* (2013.01); *A61B 6/0457* (2013.01); *A61B 6/58* (2013.01); *A61B 6/503* (2013.01)

(58) Field of Classification Search
  None
  See application file for complete search history.

(56) References Cited

U.S. PATENT DOCUMENTS

| | | | |
|---|---|---|---|
| 5,486,700 A | 1/1996 | Silberklang et al. | |
| 7,531,807 B2 | 5/2009 | Hefetz | |
| 7,557,352 B2 | 7/2009 | Hefetz | |
| 7,723,688 B2 | 5/2010 | Hefetz | |
| 2007/0053486 A1 | 3/2007 | Zelnik et al. | |
| 2007/0176106 A1* | 8/2007 | Hefetz | 250/363.02 |
| 2009/0274271 A1* | 11/2009 | Pfister et al. | 378/62 |

* cited by examiner

*Primary Examiner* — Unsu Jung
*Assistant Examiner* — Michael N Fisher
(74) *Attorney, Agent, or Firm* — Dean D. Small; The Small Patent Law Group, LLC (57) ABSTRACT

Methods and systems for patient alignment for nuclear medicine imaging are provided. One method includes activating a proximity sensor system associated with imaging detectors of the diagnostic imaging system, wherein the imaging detectors are in an L-mode configuration. The method also includes initiating movement of a patient table of the diagnostic imaging system and using a sensed proximity of a patient on the moving patient table by the proximity sensor system to automatically adjust a height of the patient table on which the patient is supported to a patient table height scanning position.

18 Claims, 6 Drawing Sheets

METHODS AND SYSTEMS FOR PATIENT ALIGNMENT FOR NUCLEAR MEDICINE IMAGING

BACKGROUND OF THE INVENTION

The subject matter disclosed herein relates generally to diagnostic imaging systems, and more particularly to methods and systems for aligning patients within the diagnostic imaging systems, especially nuclear medicine (NM) imaging systems.

Diagnostic nuclear imaging is used to study radionuclide distribution in a subject, such as a patient. Typically, one or more radiopharmaceuticals or radioisotopes are injected into the patient. Gamma imaging detector heads, typically including a collimator, are placed adjacent to a surface of the subject to monitor and record emitted radiation. The gamma imaging detector heads then may be rotated around the patient to monitor the emitted radiation from a plurality of directions, such as for cardiac imaging. The monitored radiation data from the plurality of directions is reconstructed into a three-dimensional (3D) image representation of the radiopharmaceutical distribution within the patient or a region of interest (ROI).

Generally, the resolution of a gamma imaging detector head degrades with increasing distance between the imaged object or ROI (e.g., organ) and the detector. Therefore, it is desirable to place the gamma imaging detector head as close as possible to the patient to facilitate minimizing the loss of resolution. Typically, a manual user setup procedure is performed wherein the patient table is moved in proximity to the image detectors to set a scan position for the table and determine a contour of rotation for the detectors based on a user visual inspection. This process requires significant user input and interaction, which is time consuming. Moreover, the accuracy of the setup may be affected by the level of operator experience and the amount of time the operator takes to perform the setup. Accordingly, less than optimal settings may result. Additionally, improper settings can result in image degradation or contact with the patient during imaging, which causes interruption of the image acquisition, thereby adding time to the scan.

BRIEF DESCRIPTION OF THE INVENTION

In accordance with one embodiment, a method for scan setup for a diagnostic imaging system is provided. The method includes activating a proximity sensor system associated with imaging detectors of the diagnostic imaging system, wherein the imaging detectors are in an L-mode configuration. The method also includes initiating movement of a patient table of the diagnostic imaging system and using a sensed proximity of a patient on the moving patient table by the proximity sensor system to automatically adjust a height of the patient table on which the patient is supported to a patient table height scanning position.

In accordance with another embodiment, a non-transitory computer-readable storage medium for automatically setting a patient table height for a nuclear medicine (NM) imaging system is provided. The non-transitory computer-readable storage medium has instructions for controlling a patient table and a pair of imaging detectors of the NM imaging system to move the patient table and the pair of imaging detectors to a start setup position, wherein the pair of imaging detectors are in an L-mode configuration. The non-transitory computer-readable storage medium also has instructions for automatically moving the patient table or pair of imaging detectors relative to a patient supported on the patient table and sensing a proximity detection of the patient in a near proximity detection position and a far proximity detection position during movement of the patient table or pair of imaging detectors. The non-transitory computer-readable storage medium further has instructions for using the sensed proximity detections to automatically adjust a position of at least one of the patient table or the imaging detectors to determine a centered table height and setting as a scanning position for the table, the centered table height.

In accordance with yet another embodiment, a nuclear medicine (NM) imaging system is provided that includes a gantry and a pair of imaging detectors in an L-mode configuration rotatably mounted to the gantry, wherein the pair of imaging detectors are configured to move toward and away from an examination axis of the gantry. The NM imaging system also includes a proximity sensor system associated with the pair of imaging detectors and a patient table for supporting a patient and configured to be moved vertically upward and downward. The NM imaging system further includes a processor configured to control movement of the patient table and the pair of imaging detectors to automatically adjust a position of at least one of the patient table or one or both of the imaging detectors to determine a centered patient table height based on proximity detections by the proximity sensor system.

DETAILED DESCRIPTION OF THE INVENTION

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide methods and systems to automatically perform a system setup to align a patient within a diagnostic imaging system, particularly a nuclear medicine (NM) imaging system. For example, the various embodiments may automatically determine during a setup procedure a patient table height scanning position and/or a radius of rotation for the detectors of the NM imaging system. The various embodiments may be implemented in connection with different types of imaging systems, for example, a single photon emission computed tomography (SPECT) or a gated SPECT (GSPECT) imaging system. However, the various embodiments may be implemented in connection with different medical imaging systems or non-medical imaging systems.

By practicing various embodiments and one technical effect of at least some embodiments is an automated scan setup for NM imaging. The automated scan setup automatically determines the patient table height scanning position and/or the radius of rotation for the detectors. In some embodiments, an optimized set up mode is provided to determine a patient table height and a radius of rotation that reduces or minimizes the distance between the imaging detectors (e.g., gamma imaging detector heads) and the patient during the scan. For example, the various embodiments set the patient table height and/or a radius of rotation such that during the scan, for example during a SPECT acquisition, the detectors rotate about the patient at as close a possible radius to the patient while avoiding contact with the detectors during the scan (e.g., avoiding contact with the pressure sensitive device (PSD)), which would halt the scan.

Figure 1:
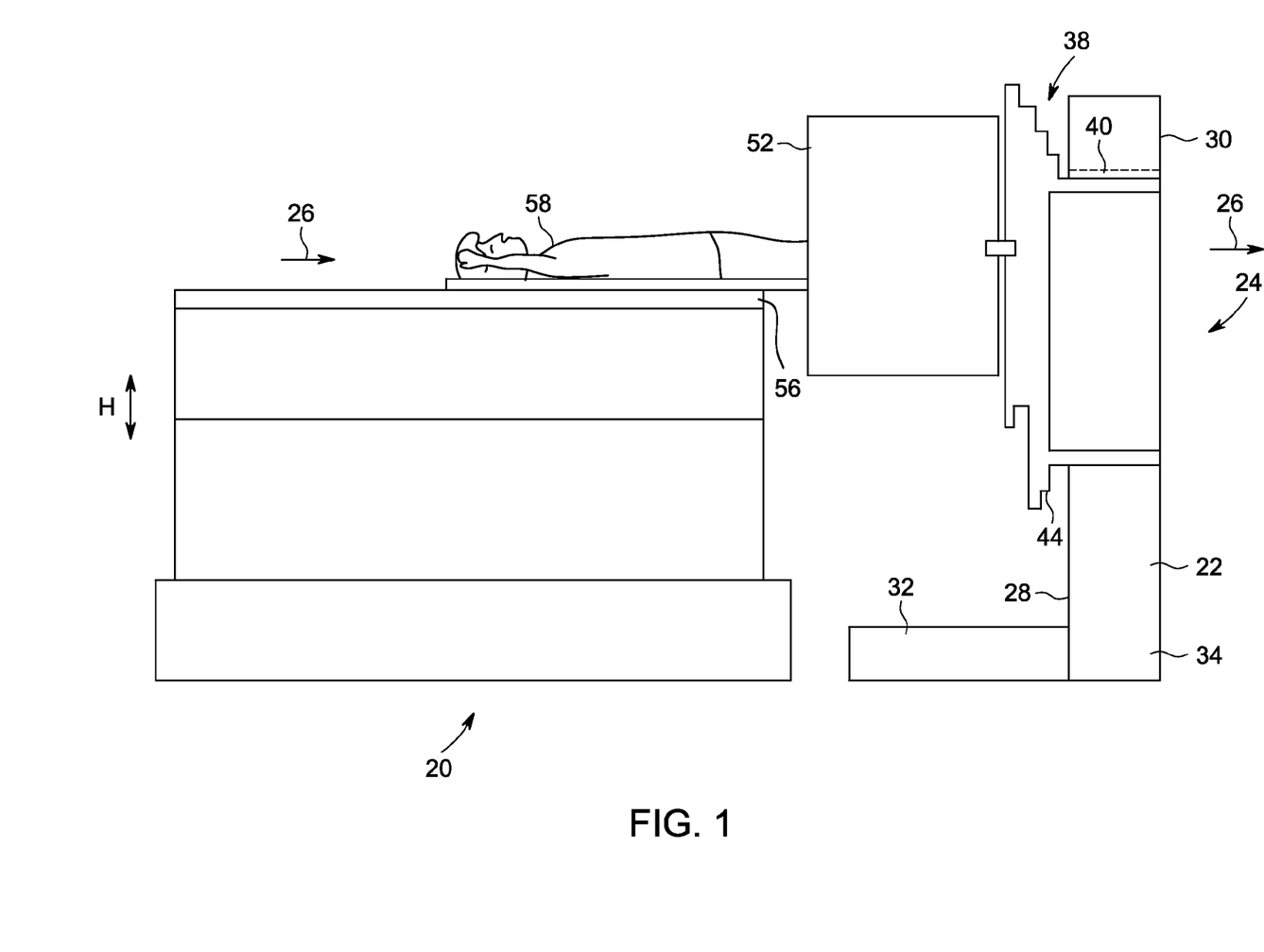
FIG. 1 is a side elevation view of a nuclear medicine (NM) imaging system in connection with which various embodiments may be implemented.
Figure 2:
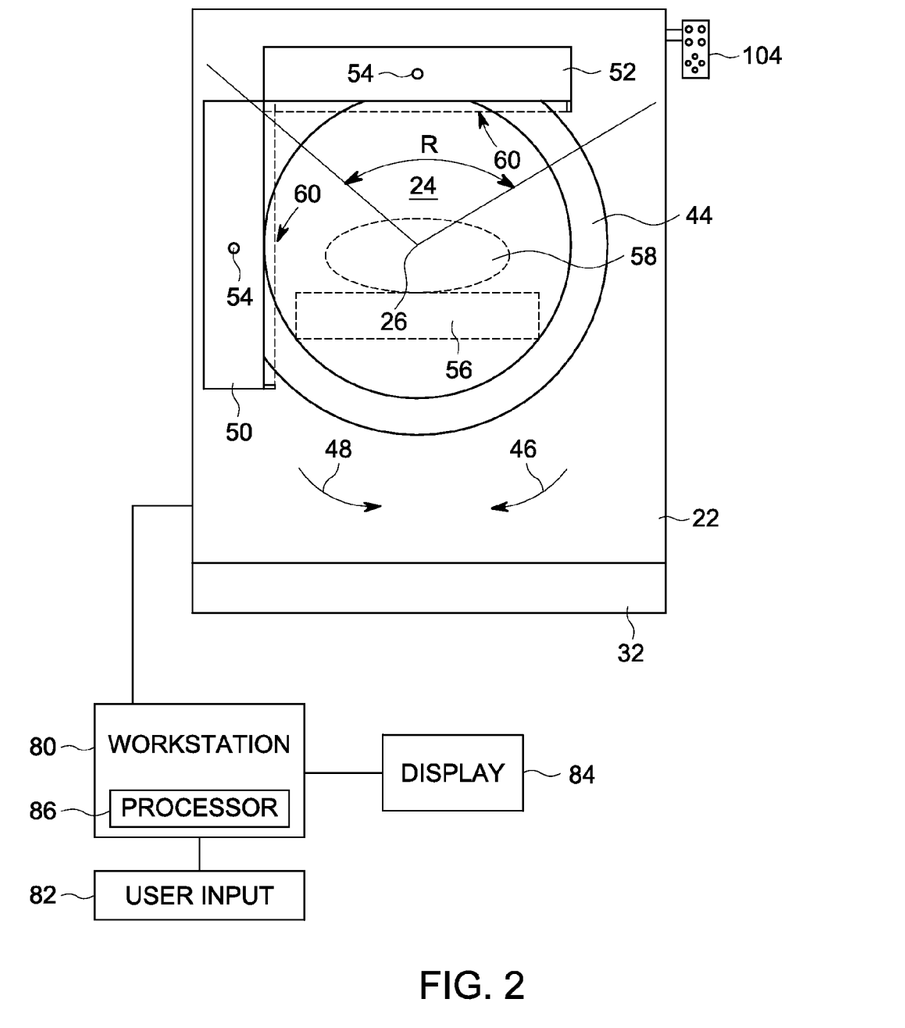
FIG. 2 is a front elevation view of the NM imaging system of FIG. 1.

FIG. 1 is a side elevation view of an NM imaging system 20 in connection with which various embodiments may be implemented. FIG. 2 is a front elevation view of the NM imaging system 20 (with the table and patient not shown). The NM imaging system 20 includes a gantry 22 with a bore 24 therethrough. A longitudinal axis 26 of bore 24 is oriented substantially perpendicular to gantry 22. In the exemplary embodiment, the bore 24 is circular and extends from a front side 28 of the gantry 22 to a backside 30 of the gantry 22. In the exemplary embodiment shown in FIG. 1, the gantry 22 includes a base having a foot portion 32 extending orthogonally from a lower end 34 of the gantry 22. The foot portion 32 may be sized and shaped to provide the gantry 22 with a stable platform such that a center of gravity of the gantry 22 remains located within a footprint of the gantry 22.

A rotor 38 is rotatably coupled to the gantry 22 adjacent to and/or within bore 24. The rotor 38 may include an annular portion coupled to an inner surface 40 of the bore 24. The annular portion extends axially toward the backside 30, at least partially into the bore 24 and extends axially toward front side 28 to a mounting ring 44 of the gantry 22. The rotor 38 is rotatable with respect to the gantry 22 using, for example, a chain and sprocket drive coupled to a motor (not shown) internal to the gantry 22, a rack and pinion configuration, and/or a worm and toothed gear arrangement, among others. The rotor 38 may be rotatable in a clockwise (CW) direction 46 and/or a counter clockwise (CCW) direction 48 (as observed from a detector side of the gantry 22), or may be rotatable in only one of the directions 46 and 48 using slip rings and/or other wireless power and communication paths to transmit electrical power and communication and data signals between the rotor 38 and the gantry 22. The mounting ring 44 rotates with respect to the gantry 22. One or more braces, brackets, or frames also may be coupled directly or indirectly to the mounting ring 44. These components operate to allow translatable, as well as rotatable operation, which may be accomplished using a screw drive, hydraulic and/or pneumatic piston or other actuator.

A pair of imaging detectors, such as radiation detectors, illustrated as gamma imaging detector heads 50 and 52, is connected to the mounting ring 44, for example, via one of more of the braces, brackets, or frames, and via pivot joints 54. Thus, the gamma imaging detector heads 50 and 52 are rotatably coupled to allow the gamma imaging detector heads 50 and 52 to rotate about the longitudinal axis 26 of the pivot joints 54. The gamma imaging detector heads 50 and 52 may be rotated manually and fixed in place before each imaging scan, or may be rotated automatically during any portion of an imaging scan using an actuator (not shown). The gamma imaging detector heads 50 and 52 may be fixed during an imaging scan. In the exemplary embodiment, the gamma imaging detector heads 50 and 52 may each be configured to rotate approximately 180 degrees in the directions 46 and 48. In an alternative embodiment, the gamma imaging detector heads 50 and 52 may each be configured to rotate approximately ninety degrees in the directions 46 and 48. In some embodiments the described herein the gamma imaging detector heads 50 and 52 rotate such that the imaging detector head 52 as illustrated in FIG. 2 has a range of rotation shown by the arrow R in FIG. 2 with the lines defining a position of a middle of the imaging detector head 52. It should be noted that the gamma imaging detector heads 50 and 52 in FIG. 2 are illustrated in an L-mode configuration, such as for a cardiac scan and the gamma imaging detector head 50 moves likewise with the gamma imaging detector head 52 along the range of rotation.

In operation, the gamma imaging detector heads 50 and 52 may rotate about the longitudinal axis 26 during rotation of the rotor 38. In various embodiments, the gamma imaging detector heads 50 and 52 may be positioned to define a radius of rotation about a patient.

With the NM imaging system 10 positioned in the L-mode and a patient table 56 (which may have mattress (not shown) thereon) having a subject, such a patient 58 to be scanned positioned thereon, an automatic table height adjustment as described in more detail herein may be performed. For example, a patient table height and a radius of rotation may be automatically determined using one or more proximity sensors.

Figure 3:
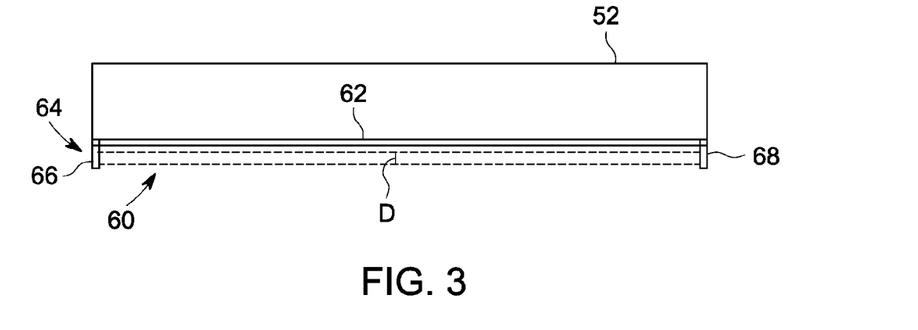
FIG. 3 is a side elevation view of a detector of the NM imaging system of FIG. 1 illustrating proximity sensors in combination with the detector.

More particularly, proximity sensors as illustrated in FIG. 3 are also provided in combination with the gamma imaging detector heads 50 and 52 as illustrated in FIG. 1 (showing only one gamma imaging detector head 50) and FIG. 2 (showing both gamma imaging detector heads 50 and 52). In particular, a proximity sensor system 60 is associated with the gamma imaging detector head 50, with a similar proximity sensor system 60 associated with the gamma imaging detector head 52. In one exemplary embodiment, each proximity sensor system 60 includes three sensor elements. In alternative embodiments, the proximity sensor systems 60 may include more or less than three sensor elements. Specifically, a pressure sensitive safety device 62 (also referred to as a PSD) of each proximity sensor system 60 may be configured to deactivate movement or automatic control of the moving parts of the NM imaging system 20, for example the rotor 38 or other moving components, such as the components changing the orientation of the first and second gamma imaging detector heads 50 and 52, when the pressure sensitive safety device 62 contacts a subject (not shown in FIG. 3) being scanned. After the pressure sensitive safety device 62 detects contact with the subject or other object, the NM imaging system 20 stops movement of all moving parts of the NM imaging system 20. Thereafter, control of the moving parts may be restricted to manual control and motion that may bring the gamma imaging detector head 50 and/or 52 nearer to the subject being scanned may be restricted, even in manual control, until contact between the pressure sensitive safety device 62 and the subject is corrected.

Additionally, a proximity sensor arrangement 64 may be included, which may operate as a near proximity sensor and a far proximity sensor. Additionally, separate proximity sensors may be included to separately provide the functionality of the near proximity sensor and the far proximity sensor. The proximity sensor arrangement 64 may be configured to stop motion of the moving parts of the NM imaging system 20. For example, the near proximity detection may be configured to stop the motion of moving parts in the direction toward the subject. In the exemplary embodiment, this proximity detection may be provided by a row of light emitting diodes (LEDs) 66 and photo-diodes 68 extending along opposite edges of the face of the gamma imaging detector heads 50 and 52 that extend, for example, approximately one centimeter (cm) from the pressure sensitive safety device 62. Additionally, the far proximity detection may be configured to stop the motion of the moving parts away from the subject, and likewise may be based on detection by the LEDs 66 and photo-diodes 68. For example, the far proximity detection may be provided by the LEDs 66 and photo-diodes 68 (or different LEDs and photo-diodes) extending along opposite edges of the face of the gamma imaging detector heads 50 and 52 that extend, for example, approximately two centimeters from the pressure sensitive safety device 62. In the exemplary embodiment, the near proximity detection and far proximity detection together define a desired or optimum distance range D between the face of the gamma imaging detector head 50 or 52 and the subject, which facilitates operation of the gamma imaging detector heads 50 and 52. Thus, a proximity sensing area along a front face of the gamma imaging detector heads 50 and 52 may be generated to define a near proximity position and a far proximity position. It should be noted that other methods of proximity detection, for example, capacitive or ultrasonic proximity sensing may be used in addition to or as an alternative to optical proximity sensing.

In an automatic body-contouring mode of operation, the movement of the moving parts in a direction away from the subject is not stopped or restricted by the near proximity detection and the movement of the moving parts in a direction toward the subject is not stopped or restricted by the far proximity detection. One example of the body-contouring mode of operation is described in U.S. Pat. No. 7,531,807, which is commonly owned.

Referring again to FIGS. 1 and 2, the patient 58 is generally positioned such that a region of interest, for example, a heart, is substantially aligned within the view of the gamma imaging detector heads 50 and 52. To facilitate maintaining the gamma imaging detector heads 50 and 52 in relatively near proximity to the region of interest, the patient table 56 may be configured to be moved in a table up direction and a table down direction with respect to gantry 22 to adjust a height (illustrated by the H arrow in FIG. 1) of the patient 58. The position illustrated with the gamma imaging detector heads 50 and 52 oriented in the L-mode configuration shown in FIG. 2 illustrates that none of the sensor elements of the proximity sensor systems 60 (shown in FIG. 3) are close enough to the patient 58 to be actuated. Movement of the patient table 56 may be subject to controls and restrictions similar to the moving parts of the NM imaging system 20 such that when the pressure sensitive safety device 62 is actuated, motion of the patient table 56 may be stopped and only permitted to move in a direction that moves the gamma imaging detector heads 50 and 52 away from the patient 58 using manual control and automatic control may be suspended.

During a setup mode of operation and/or during an imaging scan, for example, but not limited to a SPECT imaging scan, the gamma imaging detector heads 50 and 52, and/or the patient table 56, may be controlled and moved. For example, various embodiments automatically determine during the setup mode, a patient table height scanning position and/or a radius of rotation for the gamma imaging detector heads 50 and 52. Moreover, during scanning operation the rotation of the gamma imaging detector heads 50 and 52 may be controlled by controlling the rotation of rotor 38 and is generally controlled to provide step movement of several degrees (e.g., approximately three degrees) from one imaging position to the next. Accordingly, the patient 58 may be viewed by the gamma imaging detector heads 50 and 52 from a plurality of imaging positions extending, for example, 90 degrees, 180 degrees, 360 degrees, or in continuous rotation about the longitudinal axis 26.

For example, for a cardiac scan, the height of the patient table and/or the radius of rotation for the gamma imaging detector heads 50 and 52 in the L-mode are automatically determined and set during the setup mode, and thereafter a ninety degree scan of the patient 58 is performed by controlling motion of the rotor 38.

It should be noted that the NM imaging system 20 may be connected to a controller or user console, for example, a workstation 80. The workstation 80 is connected to a user input 82 for receiving user inputs (e.g., user commands) and a display 84 for displaying images of the patient 58 acquired by the NM imaging system 20. Additionally, a processor 86 is provided that may operate to perform the automatic setup and/or scanning as described in more detail herein.

Figure 4:
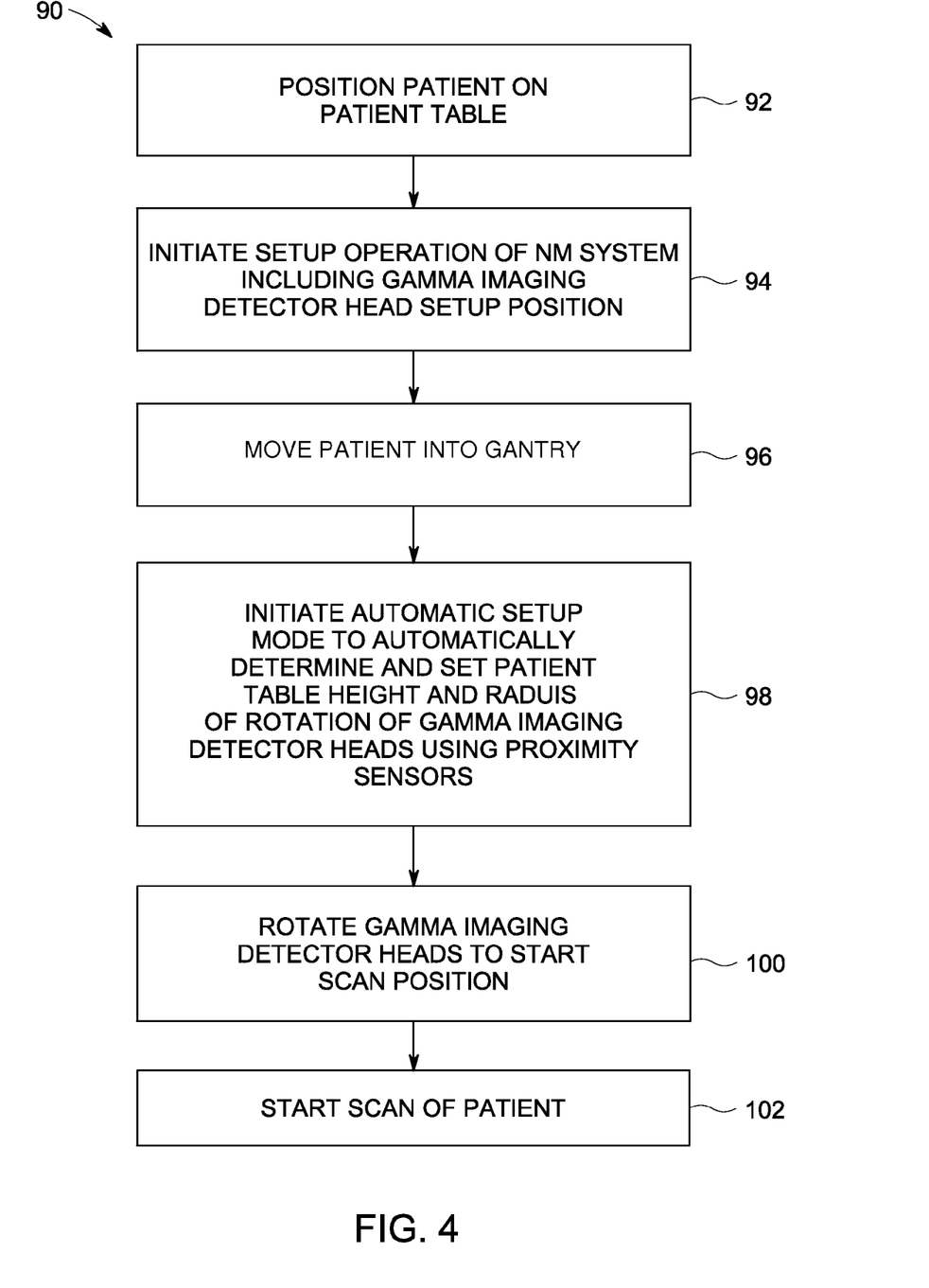
FIG. 4 is a flowchart of method for setting a patient table height scanning position and/or a radius of rotation for the detectors of an NM imaging system.

A method 90 for automatic scanning setup is shown in FIG. 4, which in various embodiments, automatically determines the patient table height scanning position and/or a radius of rotation for the gamma imaging detector heads, such as the gamma imaging detector heads 50 and 52. For example, the method determines the settings for scanning such that the gamma imaging detector heads are positioned as close to the patient as possible without causing a near proximity detection (e.g., a patient being too close to a gamma imaging detector head) or contact with a PSD.

Figure 5:
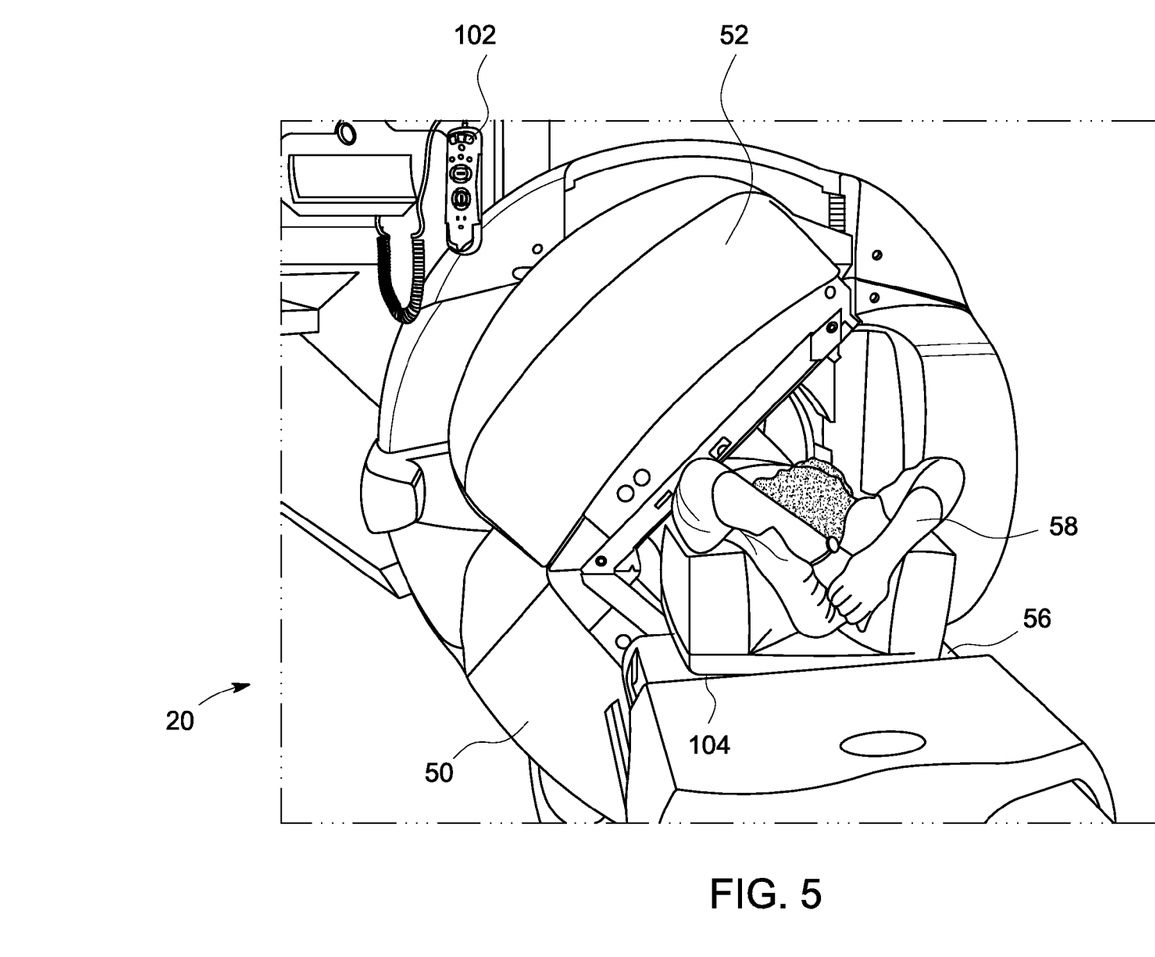
FIG. 5 is a perspective view of an NM imaging system in a setup configuration in accordance with various embodiments.

The method 90 includes positioning a patient on a patient table at 92, which may include a patient lying on the patient table with his or her arms above his or her head. Thereafter, setup operation of the NM imaging system is initiated at 94, which may include the automatic positioning of the gamma imaging detector heads at a fixed orientation or gantry angle (as shown in FIG. 5), which is a setup position. In this position, the patient is moved into the bore of the gantry at 96 and as illustrated in FIG. 5. For example, a stretcher portion of the patient table may extend into the bore such that the chest region of the patient, and in particular, the heart region of the patient, is generally aligned with the field of views of the gamma imaging detector heads. This movement of the patient into the bore may be performed manually or automatically. When performed manually, a user may operate a controller, such as the controller 104 (shown in FIGS. 2, 5 and 6) to manually adjust the movement of the stretcher and/or the patient table.

It should be noted that in this setup position (or start position) of the NM imaging system, the gamma imaging detector heads in the L-mode are aligned generally at a left side of the patient (heart side) with a portion of one gamma imaging detector head generally above the patient and a portion of the other gamma imaging detector head generally below the patient. Thus, the gamma imaging detector heads are positioned such that the midpoint between the gamma imaging detector heads is at about a side of the patient (a 270 degree position). Moreover, the arms of the patient are generally positioned above the head of the patient, which may be supported using a support member 104.

Thereafter, an automatic setup mode is initiated at 96 wherein the patient table height scanning position and/or a radius of rotation for the gamma imaging detector heads are automatically determined as described in more detail below. In general, the patient table height scanning position and/or a radius of rotation for the gamma imaging detector heads are determined using proximity sensors associated with each of the gamma imaging detector heads. For example, the proximity sensors may detect a near proximity position and a far proximity position. In various embodiments, the table height and the radius of rotation for the gamma imaging detector heads is determined by adjusting the table height and/or moving the gamma imaging detector heads to a position for the patient to be scanned such that the patient is further away from the gamma imaging detector heads than the near proximity position, but closer than the far proximity position, thereby defining a scanning position. It should be noted that this operation may be performed iteratively.

As another example, after the patient table is positioned in a setup position, the table is raised and/or lowered and/or the gamma imaging detector heads are moved until there are both near and far proximity detections. Thereafter, the positioning of the patient table and/or gamma imaging detector heads is adjusted accordingly as described in more detail below. The movement of the patient table upward and downward and/or the movement of the gamma imaging detector heads may be performed incrementally or in a continuous motion. Additionally, the speed at which the table moves up or down and/or the movement of the gamma imaging detector heads may be constant or varied. For example, the patient table may move at one speed until there is a far proximity detection and then at a slower speed until there is a near proximity detection.

Figure 6:
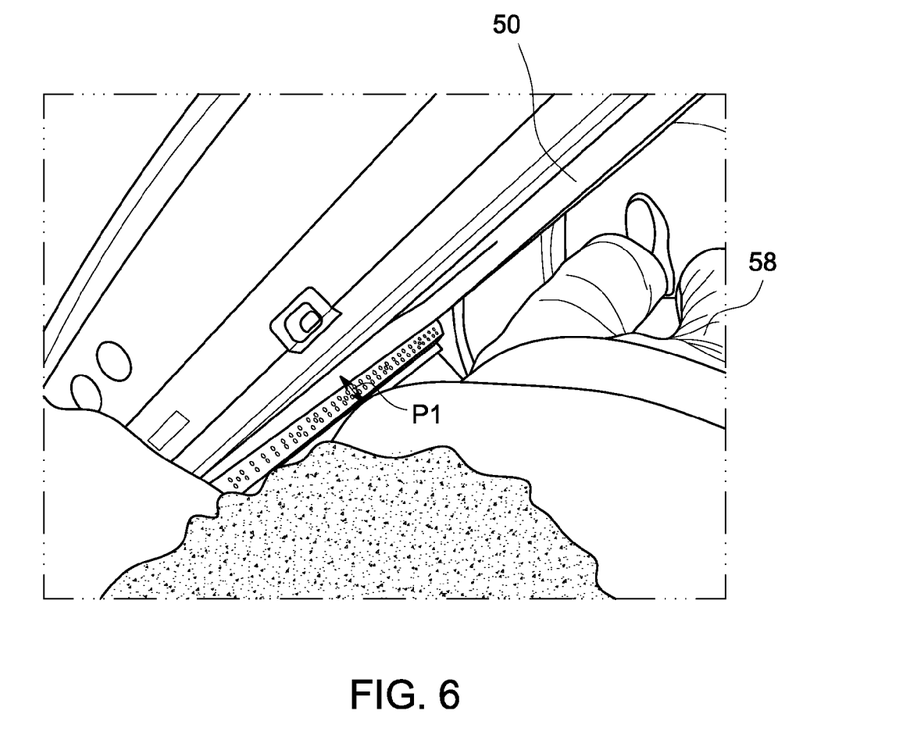
FIG. 6 is a diagram illustrating a distance determination between a detector and a patient in the setup configuration in accordance with various embodiments.
Figure 7:
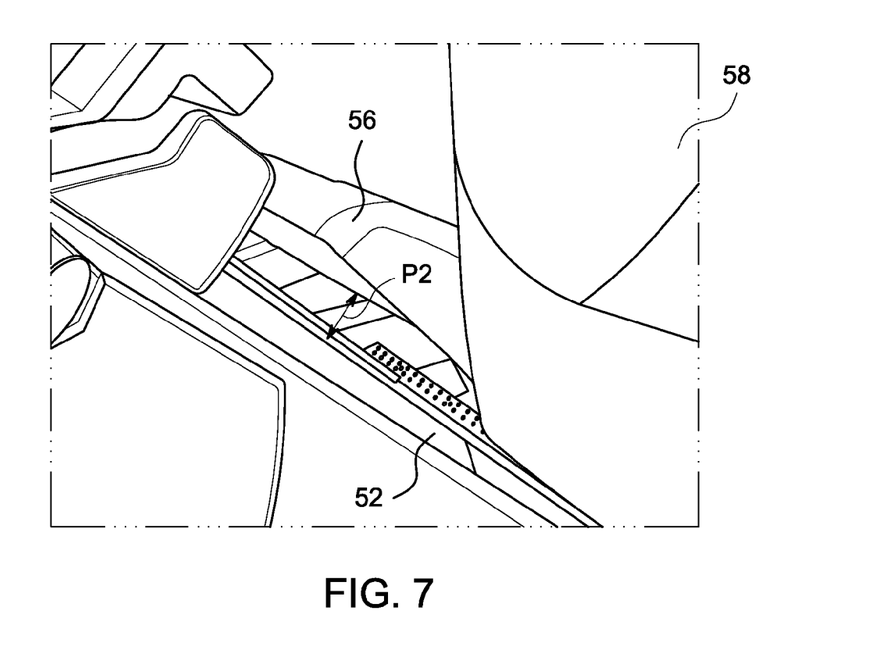
FIG. 7 is a diagram illustrating another distance determination between a detector and a patient in the setup configuration in accordance with various embodiments.

Thus, as illustrated in FIGS. 6 and 7, showing one gamma imaging detector head generally above the patient and another gamma imaging detector head generally below the patient, respectively, the proximity sensors are used to determine a position for the patient table and the gamma imaging detector heads that satisfies the scanning position criteria described above (e.g., near and far proximity detections). The position and distance of the gamma imaging detector heads in this scanning position is illustrated by the arrows P1 and P2, respectively, illustrating a desired or optimal position from the patient and the patient table, respectively.

Figure 8:
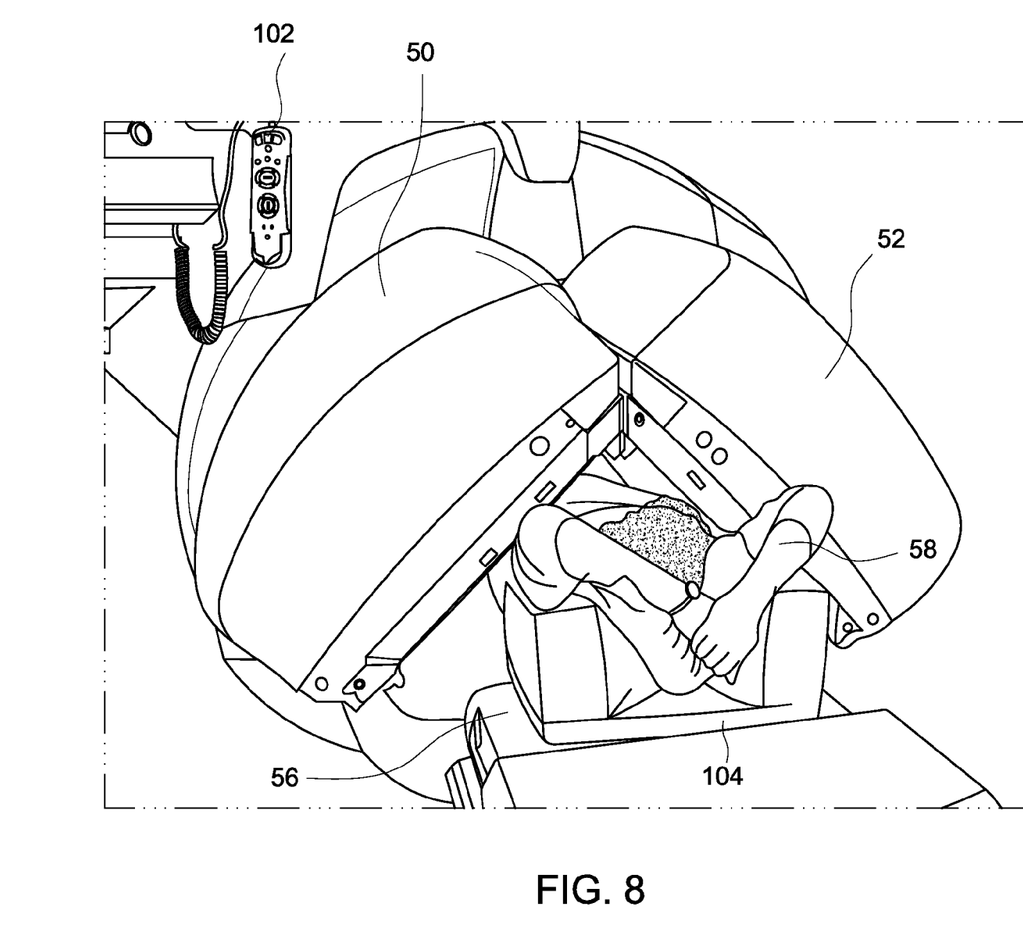
FIG. 8 is a perspective view of the NM imaging system of FIG. 3 in a start scan configuration in accordance with various embodiments.

The clearance of the gamma imaging detector heads with the patient then may be checked by rotating the gamma imaging detector heads to a start scan position as illustrated in FIG. 8. In this position, the gamma imaging detector heads are both generally positioned above and extending to the sides of the patient. Thereafter, at 100 the gamma imaging detector heads are rotated to a start scan position (as shown in FIG. 8) and the scan is started at 102 to acquire images of the patient, for example, in a cardiac perfusion study. It should be noted that the distance from the patient throughout the scan, which may encompass ninety degrees around the patient, may be controlled using an automatic body contouring process as described above, which also uses the proximity sensors. The scan may include, for example, rotating the gamma imaging detector heads ninety degrees counter-clockwise from the start position.

Thus, various embodiments provide an automatic patient position setup, which determines a patient table height and/or a radius of rotation for the gamma imaging detector heads. For example, an automated scan setup for SPECT/GSPECT scans in an L-mode may be provided, such as for cardiac perfusion scans. In various embodiments, an improved or optimized table height is automatically determined when the gamma imaging detector heads are positioned in one of the lateral side positions (e.g., 90 degree or 270 degree position), using proximity sensors as described herein.

A user interface may be provided to allow a user to select an automated setup mode, such as by selecting a <SET> function, which moves the gamma imaging detector heads to the end scan angle (setup angle). When the automatic body contouring function is selected, the gamma imaging detector heads also move toward the patient body in a contour following manner. Thereafter, a user may select a <GO> function, when the gamma imaging detector heads are in the end angle, which initiates the following actions that are performed automatically:

1. Detectors move radially in until at least one of the automatic body contour (proximity) sensors stops the gamma imaging detector heads, unless the gamma imaging detector heads are already moved to a position adjacent the patient.

2. An automatic table height operation is performed (if selected) as described herein.

3. The gamma imaging detector heads then rotate continuously to the start angle position (as shown in FIG. 8) while the automatic body contour (ABC) function is active. During this rotation (clearance rotation), the system tracks the maximal radius and saves this radius value, which is used during the image acquisition (for optional subsequent non-ABC (fixed radius) scans).

4. When the detectors reach the start scan position, the acquisition automatically starts. If the scan is a non-ABC scan, the scan radius is the radius that was saved during the clearance rotation (Step 3 above).

It should be noted that optionally, if the scan parameters were "learned" from another scan (no ABC), the scan setup is performed without the table height determination as verification to the selected scan parameters. If the calculated radius is larger than the learned radius, the system uses the larger value for the acquisition radius (for non-ABC scans only). This operation eliminates or reduces the likelihood that the scan will stop as a result of contact with a PSD during the acquisition.

It also should be noted that optionally, if the system is interrupted during the automatic setup, for example, by the PSD or any other interruption that stops motion, the system displays an indication or prompt that allows the user to select between one of the following options in some embodiments: 1) Continue (after interruption is removed); 2) Quit; or 3) Restart (quit and apply).

Table 1 below illustrates different possible selected functions and the actions performed based on user inputs. In this table, the possible selected functions are the automatic patient table height determination (Auto-Table Height), an automatic setup wherein the system automatically rotates to a start position and angle (Automated Setup) and ABC (Body Contour) wherein the radius of rotation changes (i.e., is not fixed). It should be noted that the selecting the <GO> function is effective in various embodiments only when the axes are in a valid position to start the scan or the setup as described herein.

desired or optimal position of the patient table such that the patient is between a near proximity distance (e.g., less than 1 cm from the gamma imaging detector head) and a far proximity distance (e.g., more than 2 cm from the gamma imaging

| Use case | Auto-Table Height | Automated setup | Body Contour | Expected behavior |
|---|---|---|---|---|
| 1 | False | False | False | <SET>: All axes move to predefined scan position, (including rotation angle to the exact start angle) <GO>: Scan starts at current angle and current radius, w/o body contour during scan |
| 2 | False | False | True | <SET>: All axes move to predefined scan position, (including rotation angle to the exact start angle) <GO>: Scan starts at current angle with body contour during scan |
| 3 | False | True | False | <SET>: Table moves to predefined scan position, Detectors rotate to end scan angle <GO>: Detectors rotates to start angle using continues body contour, when start angle is reached scan starts in the maximal radius that was measured during the clearance. If <GO> was pressed in an angle that is not the end angle, the initial radius shall be also considered as candidate. |
| 4 | False | True | True | <SET>: Table moves to predefined scan position, Detectors rotate to end scan angle <GO>: Detectors rotate to start angle using continues body contour, when start angle is reached scan starts with body contour on (*) Only when rotation angle is inside scan range pressing <GO> shall be valid |
| 5 | True | False | False | Not applicable |
| 6 | True | False | True | Not applicable |
| 7 | True | True | False | <SET>: Table moves to predefined scan position, Detectors rotate to end scan angle <GO> pressed at end angle: Table height optimizer starts (detectors move in till BC, table goes up and down till optimal height is found) Continue as described in use case 3 for M3 Scan starts in the maximal radius without body contour <GO> pressed at another angle: Skip table height optimizer and continue as defined in use case 3 |
| 8 | True | True | True | <SET>: Table moves to predefined scan position, Detectors rotate to end scan angle <GO> pressed at end angle: Table height optimizer starts (detectors move in till BC, table goes up and down till optimal height is found) Continue as defined in use case 4 |

With respect to the automatic determination of the patient table height and/or the radius or rotation for the gamma imaging detector heads, various embodiments use proximity sensor and may implement an ABC mechanism as describe herein. The proximity sensors may be used to determine a detector head). It should be noted that other distances may be used for the "near" and "far" distances.

It should be noted that the automatic patient table height determination is used in connection with L-mode scans that end at an angle of 90 degrees or 270 degrees. The automatic determination starts in various embodiments when the gamma imaging detector heads are positioned in one of these angles. In various embodiments, in any other condition, the automatic determination procedure is not performed.

The automatic determination of table height in various embodiments is complete when a far proximity detection condition exists, but a near proximity detection does not exist. For example, the automatic table height determination may be satisfied when the patient is detected at the far proximity detection distance, but not at the near proximity detection distance for both of the gamma imaging detector heads. When the gamma imaging detector heads are in a 90 degree position or a 270 degree position, when the near/far proximity detections are satisfied, the scanned object, comprising the patient and the patient table is centralized in the center of rotation.

Referring now to one embodiment for automatically determining the patient table height for scanning in L mode a particular patient, the following steps may be performed:

1. Activate the proximity sensors, for example, in an ABC mode.
2. As long as none of the detectors have a proximity sensor detection of "near" state, move the detectors in toward the patient.
3. Once one of the proximity sensors detects the patient or table in "near" proximity, move the patient table toward the other direction (if the upper detector has a "near" proximity detection, move the table down and vise-versa) until the other detector has a proximity detection. Mark the length of this motion y.
4. Move the patient table back toward the first detector half way (y/2).
5. Move the detectors inward until at least one of the detectors has a proximity detection.
6. Repeat steps 3-5 as long as only one detector has a "near" proximity detection, but no more than n iterations (wherein n is a predetermined maximum value, for example, between 1-5, that defines a limit for the automatic duration).

It should be noted that the automatic table height determination process may be interrupted by different events that stops motion of the detectors. These events may include, for example, PSD activation, clutch, E-Stop, RCU, etc. When such event occurs, the system motion is stopped and the user is notified or prompted that the automatic table determination procedure has been paused. When the reason for the pausing has been resolved (e.g., PSD was released), the user can resume the setup or quit.

It also should be noted that because the table height determination procedure is followed by a rotation to the start angle, in the case where the user decides to skip this step and set the table height manually, the gamma imaging detector heads are still rotated to the start angle and start acquisition position.

The imaging system components illustrated are not limited to the specific embodiments described herein, but rather, the components may be utilized independently and separately from other components described herein. For example, the components described above may also be used in combination with other imaging systems.

Thus, various embodiments provide an automated scan setup for NM imaging. The automated scan setup uses proximity sensors and distance detections to automatically determine a patient table height for use in scanning a patient on the table, for example, a desired or optimal positioning of the patient. Additionally, a radius of rotation of the gamma imaging detector heads also may be automatically determined.

Some embodiments provide a tangible and non-transitory machine-readable medium or media having instructions recorded thereon for a processor or computer to operate an imaging apparatus to perform one or more embodiments of the methods described herein. The medium or media may be any type of CD-ROM, DVD, floppy disk, hard disk, optical disk, flash RAM drive, or other type of computer-readable medium or a combination thereof.

The various embodiments and/or components, for example, the processors, or components and controllers therein, also may be implemented as part of one or more computers or processors. The computer or processor may include a computing device, an input device, a display unit and an interface, for example, for accessing the Internet. The computer or processor may include a microprocessor and/or a Graphics Processing Unit (GPU). The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable storage medium. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for scan setup for a diagnostic imaging system, the method comprising:
   activating a proximity sensor system associated with imaging detectors of the diagnostic imaging system, wherein the imaging detectors are in an L-mode configuration;
   initiating movement of a patient table of the diagnostic imaging system; and
   automatically iteratively adjusting positions of the patient table and the imaging detectors by moving at least a first imaging detector of the imaging detectors toward the patient table until the proximity sensor system detects a first state of the first imaging detector, then moving the patient table toward a second imaging detector of the imaging detectors, until the proximity sensor system detects a first state of the second imaging detector; and after moving the patient table towards the second imaging detector, moving the patient table back towards the first detector a distance to reach a patient table height scanning position, wherein the distance is less than a distance traveled by the patient table between the first state of the first and the first state of the second imaging detectors, wherein the automatically iteratively adjusting positions and moving at least the first imaging detector toward the patient table, moving the patient table toward a second imaging detector, and moving the patient table back towards the first detector occur before starting imaging acquisition.

2. A method in accordance with claim 1 wherein using the sensed proximity of the patient comprises using the sensed first proximity detection and a sensed second proximity detection to adjust a position of at least one of the imaging detectors or the patient table.

3. A method in accordance with claim 1 wherein using the sensed proximity of the patient comprises using the sensed first proximity detection and a sensed second proximity detection to adjust a position of the patient table and at least one of the imaging detectors.

4. A method in accordance with claim 1 further comprising receiving an automated setup mode selection from a user via a user interface.

5. A method in accordance with claim 1 wherein the iterative process is performed up to a predetermined maximum number of times.

6. A method in accordance with claim 1 wherein moving the patient table comprises moving the patient table one of vertically upward or downward.

7. A method in accordance with claim 1 further comprising setting the patient table height upon the sensed proximity of the patient to the imaging detectors that include at least one of a first detection condition and a second detection condition.

8. A method in accordance with claim 1 further comprising halting the movement of the patient table upon a sensed contact with a pressure sensitive device associated with the imaging detectors.

9. A method in accordance with claim 1 further comprising automatically determining a radius of rotation for the imaging detector for performing an imaging scan based on a determined patient table height scanning position and rotation of the imaging detectors from a setup position to a start scan position.

10. A method in accordance with claim 1 wherein the imaging detectors comprise a pair of gamma detectors and a setup position for the imaging detectors to determine the patient table height scanning position is one of a 90 degree position or a 270 degree position of a gantry of the diagnostic imaging system.

11. A non-transitory computer-readable storage medium for automatically setting a patient table height for a nuclear medicine (NM) imaging system, the non-transitory computer-readable storage medium having instructions for:
   controlling a patient table and a pair of imaging detectors of the NM imaging system to move the patient table and the pair of imaging detectors to a start setup position;
   automatically moving the patient table and pair of imaging detectors relative to a patient supported on the patient table; and
   iteratively adjusting positions of the patient table and the imaging detectors by moving at least a first imaging detector of the imaging detectors toward the patient table until a sensed proximity detection of a first state of the first imaging detector, then moving the patient table toward a second imaging detector of the imaging detectors until a sensed proximity detection of a first state of the second imaging detector, and after moving the patient table towards the second imaging detector, moving the patient table back towards the first detector a distance to reach a patient table height scanning position, wherein the distance is less than a distance traveled by the patient table between the first state of the first and the first state of the second imaging detectors, wherein the automatically iteratively adjusting positions and moving at least the first imaging detector toward the patient table, moving the patient table toward a second imaging detector, and moving the patient table back towards the first detector occur before starting imaging acquisition.

12. The non-transitory computer-readable storage medium in accordance with claim 11, further comprising instructions for determining a scanning radius of rotation based on a rotation of the imaging detectors after setting the scanning position.

13. The non-transitory computer-readable storage medium in accordance with claim 11, further comprising instructions for iteratively adjusting the position of the patient table and the imaging detectors based on a sensed proximity detection by at least one of the imaging detectors.

14. The non-transitory computer-readable storage medium in accordance with claim 11, further comprising instructions for halting movement of the patient table and the imaging detectors upon detecting contact of the patient with a pressure sensitive device.

15. The non-transitory computer-readable storage medium in accordance with claim 11, further comprising instructions for determining a distance between a position of an imaging detector in a first proximity detection and a second proximity detection, and using the determined distance to move the patient table.

16. The non-transitory computer-readable storage medium in accordance with claim 15, further comprising instructions for moving the patient table one-half of the determined distance towards the imaging detector in the far proximity detection.

17. A nuclear medicine (NM) imaging system comprising:
a gantry;
a pair of imaging detectors in an L-mode configuration rotatably mounted to the gantry, the pair of imaging detectors configured to move toward and away from an examination axis of the gantry;
a proximity sensor system associated with the pair of imaging detectors, wherein the proximity sensor system includes one or more proximity sensors;
a patient table for supporting a patient and configured to be moved vertically upward and downward; and
a processor configured to control movement of the patient table and the pair of imaging detectors by automatically iteratively adjusting positions of the patient table and the imaging detectors by moving at least a first imaging detector of the imaging detectors toward the patient table until the proximity sensor system detects a first state of the first imaging detector, then moving the patient table toward a second imaging detector of the imaging detectors, until the proximity sensor system detects a first state of the second imaging detector; and after moving the patient table towards the second imaging detector, moving the patient table back towards the first detector a distance to reach a patient table height scanning position, wherein the distance is less than a distance traveled by the patient table between the first state of the first and the first state of the second imaging detectors, wherein the automatically iteratively adjusting positions and moving at least the first imaging detector toward the patient table, moving the patient table toward a second imaging detector, and moving the patient table back towards the first detector occur before starting imaging acquisition.

18. An NM imaging system in accordance with claim 17 wherein the proximity sensor system comprise proximity sensors configured to generate a proximity sensing area along a front face of the imaging detectors to define a first proximity position and a second proximity position.

* * * * *